United States Patent
Zemach et al.

(10) Patent No.: US 11,044,884 B1
(45) Date of Patent: Jun. 29, 2021

(54) HIGH YIELD SESAME (71) Applicant: EQUI-NOM LTD, Givat Brenner (IL)

(72) Inventors: Itay Zemach, Rehovot (IL);
Menachem Sklarz, Beer Sheva (IL);
Oswald Crasta, Lubbock, TX (US)

(73) Assignee: Equi-nom Ltd

( * ) Notice: Subject to any disclaimer, the term of this patent is extended or adjusted under 35 U.S.C. 154(b) by 0 days.

(21) Appl. No.: 17/076,027

(22) Filed: Oct. 21, 2020

(51) Int. Cl.
*A01H 6/66* (2018.01)
*A01H 5/10* (2018.01)
*A01H 1/04* (2006.01)
*C12Q 1/6895* (2018.01)

(52) U.S. Cl.
CPC .............. *A01H 6/66* (2018.05); *A01H 1/04* (2013.01); *A01H 5/10* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| 7,847,149 B2 * | 12/2010 | Langham ............... A01H 5/08 800/260 |
| 10,577,623 B2 | 3/2020 | Gar et al. |
| 2020/0093087 A1 | 3/2020 | Gar et al. |

OTHER PUBLICATIONS

Wu et al. BMC Plant Biology (2014), 14:274.*
Ashri A. 1998. Sesame Breeding. In: Janick J. (ed.), Plant Breeding Reviews vol. 16, John Wiley and Sons, Somerset, NJ, pp. 179-228.

* cited by examiner

*Primary Examiner* — Medina A Ibrahim
(74) *Attorney, Agent, or Firm* — Zeev Pearl; Pearl Cohen Zedek Latzer Baratz LLP (57) ABSTRACT

High yield sesame plants and parts thereof are provided. Phenotypic and genotypic analysis of many sesame varieties was performed to derive markers for phenotypic traits that contribute to high yield, and a breeding simulation was used to identify the most common and most stable markers. Examples for such phenotypic traits include the number of capsules per leaf axil, the capsule length, the height to first capsule and the number of lateral shoots. Following verification of trait stability over several generations, markers and marker cassettes were defined as being uniquely present in the developed sesame lines. The resulting high yield, shatter-resistant sesame lines can be used to increase sesame yield for its various uses.

11 Claims, 4 Drawing Sheets

Specification includes a Sequence Listing.

HIGH YIELD SESAME

BACKGROUND OF THE INVENTION

1. Technical Field

The present invention relates to the field of sesame genetics and breeding, and more particularly, to quantitative trait loci (QTLs, or QTL) associated with sesame crop yield.

2. Discussion of Related Art

Sesame (*Sesamum indicum*) is an oilseed crop that is cultivated over a large range of soil and climate conditions, typically in subtropical climates, and is used for seeds, oil and paste products. Low yield varieties are commonly used, yet such varieties make sesame non-profitable to grow in developed countries.

SUMMARY OF THE INVENTION

The following is a simplified summary providing an initial understanding of the invention. The summary does not necessarily identify key elements nor limit the scope of the invention, but merely serves as an introduction to the following description.

One aspect of the present invention provides a high yield sesame plant or a part thereof, the sesame plant having shatter-resistant capsules and comprising: a plurality of loci associated with a corresponding plurality quantitative trait loci (QTLs) having a corresponding plurality of nucleic acid genetic markers that are associated with a plurality of phenotypic traits of the sesame plant, wherein the phenotypic traits comprise at least a Number of capsules per leaf axil trait, a Capsule length trait, a Number of lateral shoots trait and a Height to first capsule trait, and wherein the QTL and marker associated with the Number of capsules per leaf axil trait comprise QTL 4 with corresponding markers set forth in Seq. IDs 7 or 8.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein are for the purpose of description and should not be regarded as limiting.

Sesame plants and parts thereof are provided, which provide higher yield than current varieties. Phenotypic and genotypic analyses of many sesame varieties were performed to derive markers for high yield and other phenotypic traits, and a breeding simulation was used to identify the most common and most stable markers. Following verification of trait stability over several generations, markers and marker cassettes were defined as being uniquely present in the developed sesame lines. The resulting high yield sesame lines can be used to increase the yield of sesame crops for their various uses.

U.S. Pat. No. 10,577,623 and U.S. Patent Application Publication No. 2020/0093087 teach QTLs that confer shatter resistant capsules, and elite sesame varieties having shatter resistant capsules. Shatter resistant lines were used at least partly to further derive the disclosed high yield sesame lines disclosed herein.

Shatter resistant capsules were characterized in fully developed capsules having at most 10% seed moisture, and the shatter-resistant capsules are characterized by at least one of the features: (i) at least 80% seed retention after shaking the plant, (ii) at least 80% seed retention after the capsules are turned upside down, (iii) a ratio of at least 5:1 between a total length of the capsule and a length of a zone in which the capsule tips are open, and/or 20-30% of the capsules retain 90-95% of the seeds in fully developed green capsules before drying.

Various embodiments comprise shatter-resistant sesame plants or part(s) thereof that have high yield and comprise a plurality of loci associated with a corresponding plurality quantitative trait loci (QTLs) having a corresponding plurality of nucleic acid genetic markers that are associated with a plurality of phenotypic traits of the sesame plant.

Phenotypic and genotypic analyses of many sesame varieties were performed to derive markers for phenotypic traits that contribute to high yield, and a breeding simulation was used to identify the most common and most stable markers. Examples for such phenotypic traits include the number of capsules per leaf axil (e.g., 1 or 3), the capsule length (e.g., 15-37 mm), the height (on the plant stem) to the first capsule (e.g., 10-55 cm) and the number of lateral shoots (e.g., 0 to 12). Following verification of trait stability over several generations, markers and marker cassettes were defined as being uniquely present in the developed sesame lines. The resulting high yield sesame lines can be used to increase sesame yield for its various uses. Details concerning the QTLs and markers are provided in Table 1 below, and the methods used to develop and select the varieties are disclosed with respect to FIG. 4 below.

Figure 1:
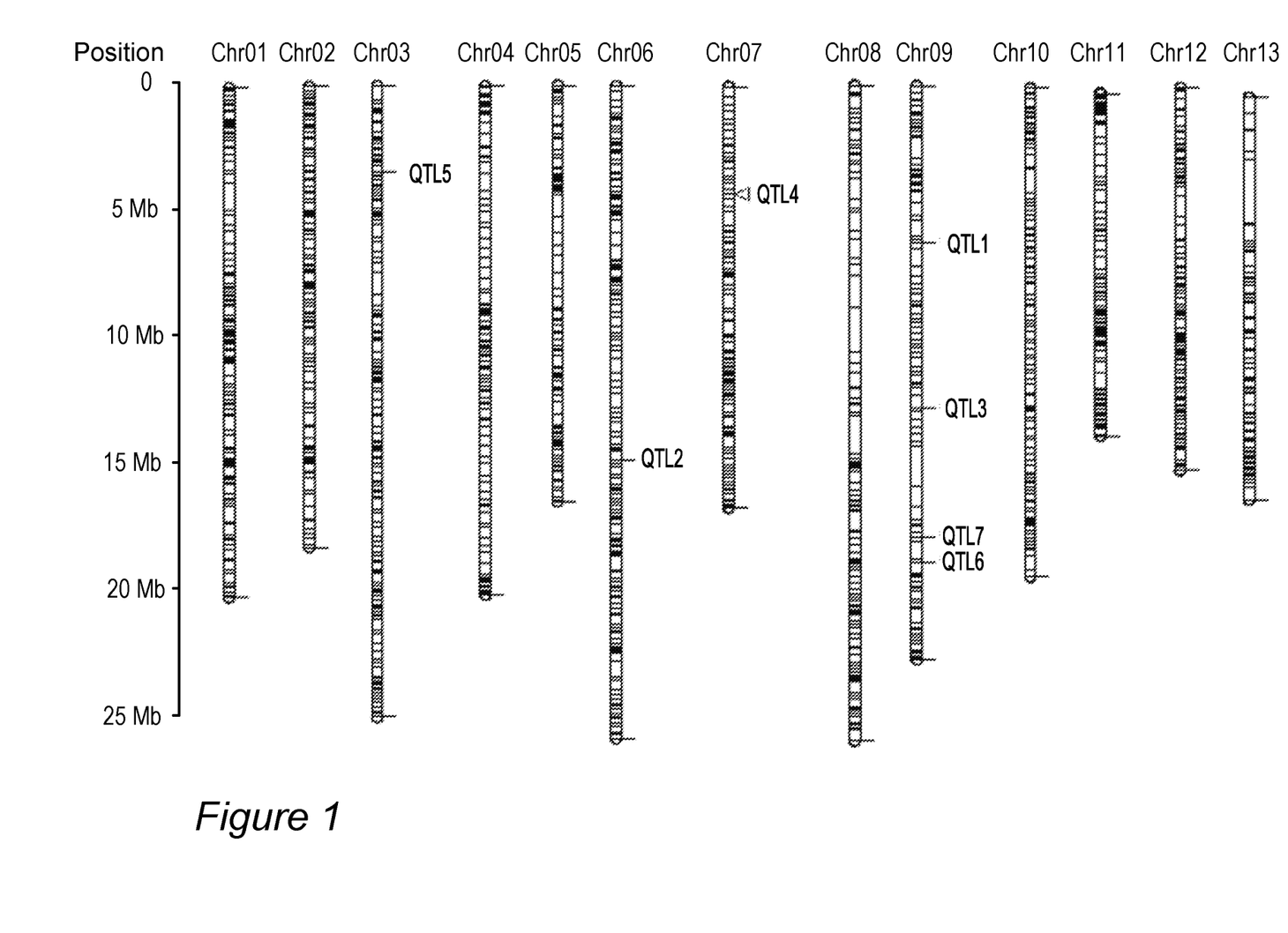
FIG. 1 is a high-level schematic illustration of sesame chromosomes with indications of the markers' loci, according to some embodiments of the invention.

FIG. 1 is a high-level schematic illustration of sesame chromosomes with indications of the markers' loci (QTL number), according to some embodiments of the invention. FIG. 1 illustrates schematically the thirteen sesame chromosomes and the marker locations indicated along them.

Table 1 provides the derived genetic markers, QTLs, corresponding traits and resulting marker cassettes, according to some embodiments of the invention.

TABLE 1

Genetic markers, QTLs, corresponding traits and marker cassettes with corresponding high yield components.

| QTL | Seq ID | MarkerID | Chromosome, Position, Strand [1] | QTL P-value | Phenotypic trait |
|---|---|---|---|---|---|
| 1 | 1,2 | MaSI0003637 | Chr9, 6319255, + | <0.05 | Capsule length |
| 2 | 3,4 | MaSI0003889 | Chr6, 14822546, + | <0.05 | Height to first capsule Capsule length |
| 3 | 5,6 | MaSI0003835 | Chr9, 12880820, + | <0.05 | Capsule length Height to first capsule Number of lateral shoots |
| 4 | 7,8 | MaSI0003448 | Chr7, 4339429, + | <0.05 | Number of capsules per leaf axil |
| 5 | 9,10 | MaSI0003358 | Chr3, 3895479, + | <0.05 | Capsule length Height to first capsule |
| 6 | 11,12 | MaSI0003838 | Chr9, 18953887, + | <0.05 | Capsule length Height to first capsule |
| 7 | 13,14 | MaSI0003635 | Chr9, 17947299, − | <0.05 | Number of lateral shoots |

Figure 2A:
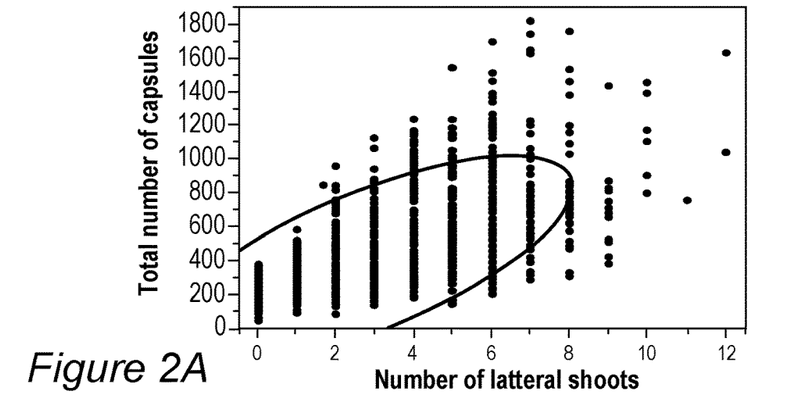
FIGS. 2A-2C present experimental results indicating the correlation between phenotypic traits and the higher yield in sesame varieties with the disclosed marker cassettes, according to some embodiments of the invention.
Figure 2B:
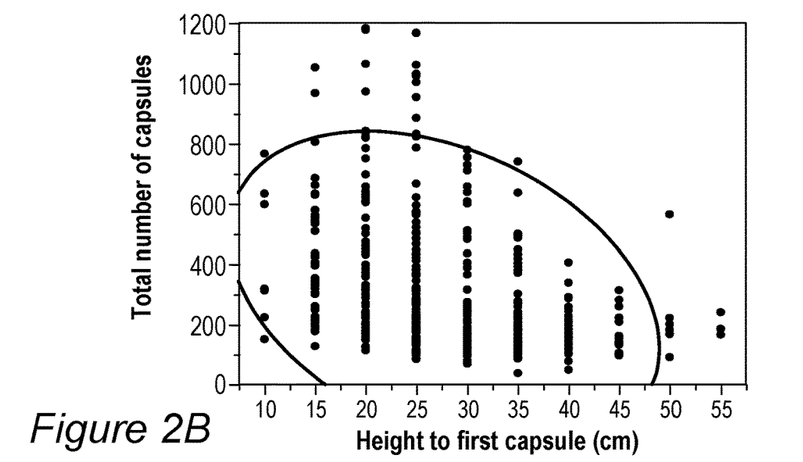
Figure 2C:
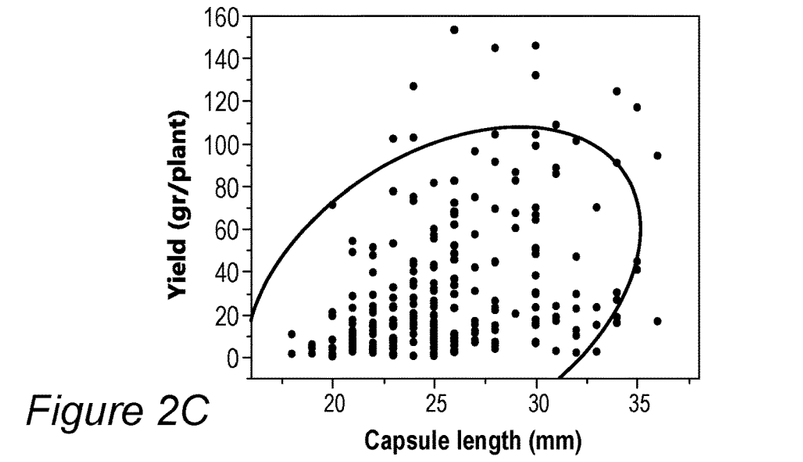

FIGS. 2A-2C present experimental results indicating the correlation between phenotypic traits and the higher yield in sesame varieties with the disclosed marker cassettes, according to some embodiments of the invention. The total number of capsules directly influences the total yield and is shown to be correlated with the phenotypic traits—Number of lateral shoots (FIG. 2A), Height to first capsule (FIG. 2B). Additionally, Capsule length is shown to be correlated with total yield (FIG. 2C). The data were collected with breeding material that included the elite lines (e.g., sesame varieties ES103, ES107, ES108, of the 2019 harvest.

Figure 3A:
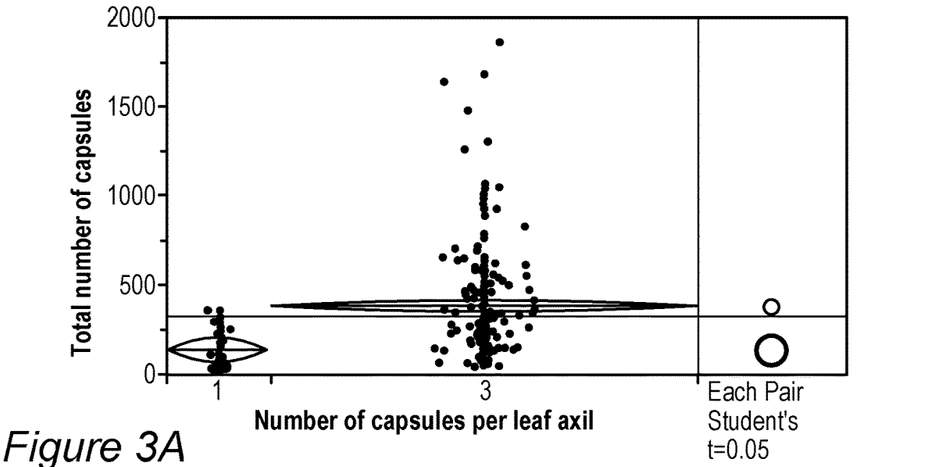
FIGS. 3A-3C present experimental results indicating the significant differences provided by the disclosed cassettes on overall yield in sesame, according to some embodiments of the invention.
Figure 3B:
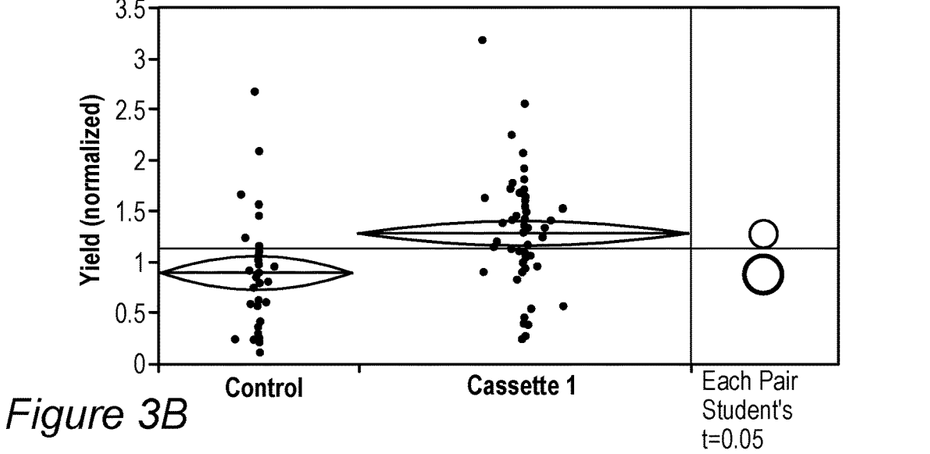
Figure 3C:
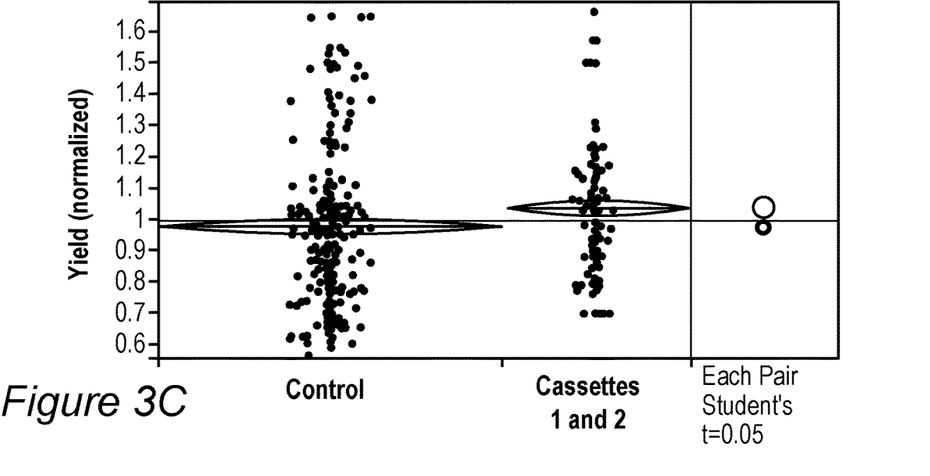

FIGS. 3A-3C present experimental results indicating the significant differences provided by the disclosed cassettes on overall yield in sesame, according to some embodiments of the invention. FIG. 3A illustrates the significant effect of QTL 4 (associated with the Number of capsules per leaf axil) on the total yield measured as total number of capsules, FIG. 3B illustrates the significant effect of cassette 1 markers on the yield (normalized with respect to the control commercial varieties grown under the same conditions and having the highest yield, including registered sesame lines ES103 and ES108) and FIG. 3C illustrates the significant effect of both cassettes (1 and 2) on the normalized yield.

In FIGS. 2A, 2B and 3A (with measured number of capsules on the y axis), each figure includes data points for single F2 plants. In FIGS. 2C, 3B and 3C (with measured yield on the y axis), each figure includes data points for groups of plants derived from self-crossed progeny of an older generation.

FIGS. 2A-2C further illustrate the corresponding bivariate normal ellipses for p=0.95. The significance of the relation between the yield and fruit length was high, for example—in FIG. 2A, correlation coefficient of 0.73 with p<0.0001 for 2230 plants; in FIG. 2B, correlation coefficient of −0.36 with p<0.0001 for 446 plants). It is noted that the Number of lateral shoots trait was significantly associated with the respective markers (P=0.15).

Advantageously, disclosed embodiments provide sesame plants with high yield that may make sesame growing profitable even in developed countries. Specifically, yield improvements of at least 10% with respect to control lines such as registered sesame lines ES103, ES107 and ES108 and up to three times the yield of the control lines.

QTL 1, as used herein, refers to a polymorphic genetic locus linked to genetic marker MaSI0003637 on sesame chromosome 9. The two alleles of marker MaSI0003637 at QTL 1 have the SNP bases "C" or "G", respectively, at position 6319255 (+strand) of Chr9, as set forth, respectively, in the nucleic acid sequences of Seq IDs 1 and 2. In cassette 1, QTL 1 may be homozygous for allele 1 (Seq ID 1) or be heterozygous (Seq IDs 1 and 2).

Seq ID No. 1 (SNP base bold):
CTATCTTTGTGATAATCCTATAAATTAAACAAAAATACCATTGACTATTG

AGATTAGAGAAAGATGCAATTTAACTCATCTAATATGAGAAATGAGTAAA

AGTGTTATGATAATTTGCTAATTCCTTTTTTGCACTGGTTTATCTGCTCA

TTTCACATAT

Seq ID No. 2 (SNP base bold):
CTATCTTTGTGATAATCCTATAAATTAAACAAAAATACCATTGACTATTG

AGATTAGAGAAAGATGCAATTTAACTCATGTAATATGAGAAATGAGTAAA

AGTGTTATGATAATTTGCTAATTCCTTTTTTGCACTGGTTTATCTGCTCA

TTTCACATAT

QTL 2, as used herein, refers to a polymorphic genetic locus linked to genetic marker MaSI0003889 on sesame chromosome 6. The two alleles of marker MaSI0003889 at QTL 2 have the SNP bases "T" or "C", respectively, at position 14822546 (+strand) of Chr6, as set forth, respectively, in the nucleic acid sequences of Seq IDs 3 and 4. In cassette 1, QTL 2 may be homozygous for allele 1 (Seq ID 3) or be heterozygous (Seq IDs 3 and 4).

Seq ID No. 3 (SNP base bold):
AGTTTTTGTTCTTAAACAGTGCATTTTTTTTTTTTGACAAAATTCATT

ATTTTCATTATCTTGCTGTCAAATATAATGAAAAAATTCATCTGAGGCTG

TTTTGAGGGTGGGAAAGAAAAACTATCATTTCCTCCCTGAAATTTAATTT

TTTGAATATTTAATCATATTCGGACAGGTGATATTTTCACATAAAAGCAA

T

Seq ID No. 4 (SNP base bold):
AGTTTTTGTTCTTAAACAGTGCATTTTTTTTTTTTGACAAAATTCATT

ATTTTCATTATCTTGCTGTCAAATATAATGAAAAAATTCATCTGAGGCTG

CTTTGAGGGTGGGAAAGAAAAACTATCATTTCCTCCCTGAAATTTAATTT

TTTGAATATTTAATCATATTCGGACAGGTGATATTTTCACATAAAAGCAA

T

QTL 3, as used herein, refers to a polymorphic genetic locus linked to genetic marker MaSI0003835 on sesame chromosome 9. The two alleles of marker MaSI0003835 at QTL 3 have the SNP bases "A" or "G", respectively, at position 12880820 (+strand) of Chr9, as set forth, respectively, in the nucleic acid sequences of Seq IDs 5 and 6. In cassette 1, QTL 3 may be homozygous for allele 1 (Seq ID 5) or be heterozygous (Seq IDs 5 and 6).

Seq ID No. 5 (SNP base bold):
AACACAAAAAACCAAACACTTTCATATGATCATAGTTAGGGGCCTTCTTA

TATAATAATTCATAGGGTGTTTTCCAACTTAATGTTTGTGTTGGAAGTCT

ATTAATTATGTATGTGGCAGCTAACAATGCCTCGGCCCAGAATCTTTGTG

GCATGTTTGCTTGGAACATCAAAGATCTAGCCCCTTGAAAAAGGTGTTGG

T

Seq ID No. 6 (SNP base bold):
AACACAAAAAACCAAACACTTTCATATGATCATAGTTAGGGGCCTTCTTA

TATAATAATTCATAGGGTGTTTTCCAACTTAATGTTTGTGTTGGAAGTCT

GTTAATTATGTATGTGGCAGCTAACAATGCCTCGGCCCAGAATCTTTGTG

GCATGTTTGCTTGGAACATCAAAGATCTAGCCCCTTGAAAAAGGTGTTGG

T

QTL 4, as used herein, refers to a polymorphic genetic locus linked to genetic marker MaSI0003448 on sesame chromosome 7. The two alleles of marker MaSI0003448 at QTL 4 have the SNP bases "T" or "C", respectively, at position 4339429 (+strand) of chromosome 7, as set forth, respectively, in the nucleic acid sequences of Seq IDs 7 and 8. In both cassettes 1 and 2, QTL 4 may be homozygous for allele 1 (Seq ID 7) or be heterozygous (Seq IDs 7 and 8).

Seq ID No. 7 (SNP base bold):
ATTTGGAGCCGGGTTCACATTGTTTCCAGCCTCTCAAAGGATTTTGGTCT

TCCAGGATTCAGGATCGGCATGATCTATTTCAACAGTAAAACCCTGATTG

CTGCTGCAACAAAAATGTCGAGTTTTGGGCTGGTCTCTTCTCAATCCCAG

TTCCTACTGT

Seq ID No. 8 (SNP base bold):
ATTTGGAGCCGGGTTCACATTGTTTCCAGCCTCTCAAAGGATTTTGGTCT

TCCAGGATTCAGGATCGGCATGATCTATTCCAACAGTAAAACCCTGATTG

CTGCTGCAACAAAAATGTCGAGTTTTGGGCTGGTCTCTTCTCAATCCCAG

TTCCTACTGT

QTL 5, as used herein, refers to a polymorphic genetic locus linked to genetic marker MaSI0003358 on sesame chromosome 3. The two alleles of marker MaSI0003358 at QTL 5 have the SNP bases "A" or "G", respectively, at position 3895479 (+strand) of Chr3, as set forth, respectively, in the nucleic acid sequences of Seq IDs 9 and 10. In cassette 2, QTL 5 may be homozygous for allele 1 (Seq ID 9) or be heterozygous (Seq IDs 9 and 10).

Seq ID No. 9 (SNP base bold):
TTAAAGTGATGAGAGTTGATGTTACTGAGAATATAAATGAGGATACTGTG

AAGCAGTTTATCGAAGAAGACAATGAGAACACAACCAGCAAGGACACCAA

AGAGGAAGTTACTGATATGGGTAACAATCAGCCAGATCGAGTTGCTGCAC

AAGGAGATAATGATGTGATGGAAGATGAAAATAATTTAGACATGAAGC

Seq ID No. 10 (SNP base bold):
TTAAAGTGATGAGAGTTGATGTTACTGAGAATATAAATGAGGATACTGTG

AAGCAGTTTATCGAAGAAGACAATGAGAACACAACCAGCAAGGACACCGA

AGAGGAAGTTACTGATATGGGTAACAATCAGCCAGATCGAGTTGCTGCAC

AAGGAGATAATGATGTGATGGAAGATGAAAATAATTTAGACATGAAGC

QTL 6, as used herein, refers to a polymorphic genetic locus linked to genetic marker MaSI0003838 on sesame chromosome 9. The two alleles of marker MaSI0003838 at QTL 6 have the SNP bases "A" or "G", respectively, at position 18953887 (+strand) of Chr9, as set forth, respectively, in the nucleic acid sequences of Seq IDs 11 and 12. In cassette 2, QTL 6 may be homozygous for allele 1 (Seq ID 11) or be heterozygous (Seq IDs 11 and 12).

Seq ID No. 11 (SNP base bold):
ATCATGAATTTTACTCCTATTTTTTTGTTAATATTAACAAATCTAGTGGA

TTTTGACTAACAAAGGGACTTATTTTATTAAACGAAAGCAACCTTCAAGG

ATATTAAATATAATTTTTCAAACCACATGAGATTTATATGCAATTACATT

AAATTTCGGTAGAGTGGAGTAGTTATCCCTAGAAATATTACAGTCGAAGT

G

Seq ID No. 12 (SNP base bold):
ATCATGAATTTTACTCCTATTTTTTTGTTAATATTAACAAATCTAGTGGA

TTTTGACTAACAAAGGGACTTATTTTATTAAACGAAAGCAACCTTCAAGG

GTATTAAATATAATTTTTCAAACCACATGAGATTTATATGCAATTACATT

AAATTTCGGTAGAGTGGAGTAGTTATCCCTAGAAATATTACAGTCGAAGT

G

QTL 7, as used herein, refers to a polymorphic genetic locus linked to genetic marker MaSI0003635 in linkage group 15 on sesame chromosome 9. The two alleles of marker MaSI0003635 at QTL 7 have the SNP bases "A" or "G", respectively, on the minus strand, at position 17947299 of Chr9, as set forth, respectively, in the nucleic acid sequences of Seq IDs 13 and 14. In cassette 2, QTL 7 may be homozygous for allele 1 (Seq ID 13) or be heterozygous (Seq IDs 13 and 14).

Seq ID No. 13 (SNP base bold):
GGAGGCAAAAGAATACGGGTTGGTTGATGCAGTGATCGATGATGGCAAGC

CTGGACTAGTCGCACCCATCGCAGATACTGCACCCCCACCAAAAACCCGT

GTCTGGGATCTTTGGAAAATCGAAGGCAGTAAAAAAGCCAAGAAAAACTT

ACCCTCCGAAGAGAAACTATTACAAAATGGATACACAGTTGGCCAAGGTG

-continued

AAGATGACAGAAGCACGGAACAGGTAGAGGAAGCACCAACATCTCAATGA

GTAATGAATGTTGAGATATTTCTTGTATACACTGTCAAACATTGTAGCTA

G

Seq ID No. 14 (SNP base bold):
GGAGGCAAAAGAATACGGGTTGGTTGATGCAGTGATCGATGATGGCAAGC

CTGGACTAGTCGCACCCATCGCAGATACTGCACCCCCACCAAAAACCCGT

GTCTGGGATCTTTGGAAAATCGAAGGCAGTAAAAAAGCCAAGAAAAACTT

GCCCTCCGAAGAGAAACTATTACAAAATGGATACACAGTTGGCCAAGGTG

AAGATGACAGAAGCACGGAACAGGTAGAGGAAGCACCAACATCTCAATGA

GTAATGAATGTTGAGATATTTCTTGTATACACTGTCAAACATTGTAGCTA

G

High yield sesame plant(s) or part(s) thereof are provided, which have shatter-resistant capsules and comprise a plurality of loci associated with a corresponding plurality quantitative trait loci (QTLs) having a corresponding plurality of nucleic acid genetic markers that are associated with a plurality of phenotypic traits of the sesame plant.

In certain embodiments, the phenotypic traits at least a Number of capsules per leaf axil trait, a Capsule length trait and a Height to first capsule trait.

The QTL and marker associated with the Number of capsules per leaf axil trait may comprise QTL 4 with corresponding markers set forth in Seq. IDs 7 or 8.

In certain embodiments, the QTLs and markers associated with the Capsule length trait may comprise QTLs 1, 2, 3 with corresponding markers set forth in Seq. IDs 1 or 2, Seq. IDs 3 or 4, Seq. IDs 5 or 6, respectively.

In certain embodiments, the QTLs and markers associated with the Height to first capsule trait may comprise QTLs 1, 3 with corresponding markers set forth in Seq. IDs 1 or 2, Seq. IDs 5 or 6, respectively.

In certain embodiments, the phenotypic traits may further comprise a Number of lateral shoots trait, and the QTL and marker associated with the Number of capsules per leaf axil trait may comprise QTL 3 with corresponding markers set forth in Seq. IDs 5 or 6.

In certain embodiments, the QTLs and markers associated with the Capsule length trait, with the Height to first capsule trait and with the Number of lateral shoots trait—may comprise QTLs 5, 6, 7 with corresponding markers set forth in Seq. IDs 9 or 10, Seq. IDs 11 or 12, Seq IDs 13 or 14—respectively.

In certain embodiments, the phenotypic traits may comprise a high yield of up to three times higher than the control variety (see, e.g., FIG. 3B). In various embodiments, the plants may be hybrids and/or the plant parts may comprise any of: a seed, an endosperm, an ovule, pollen, cell, cell culture, tissue culture, plant organ, protoplast, meristem, embryo, or a combination thereof.

Figure 4:
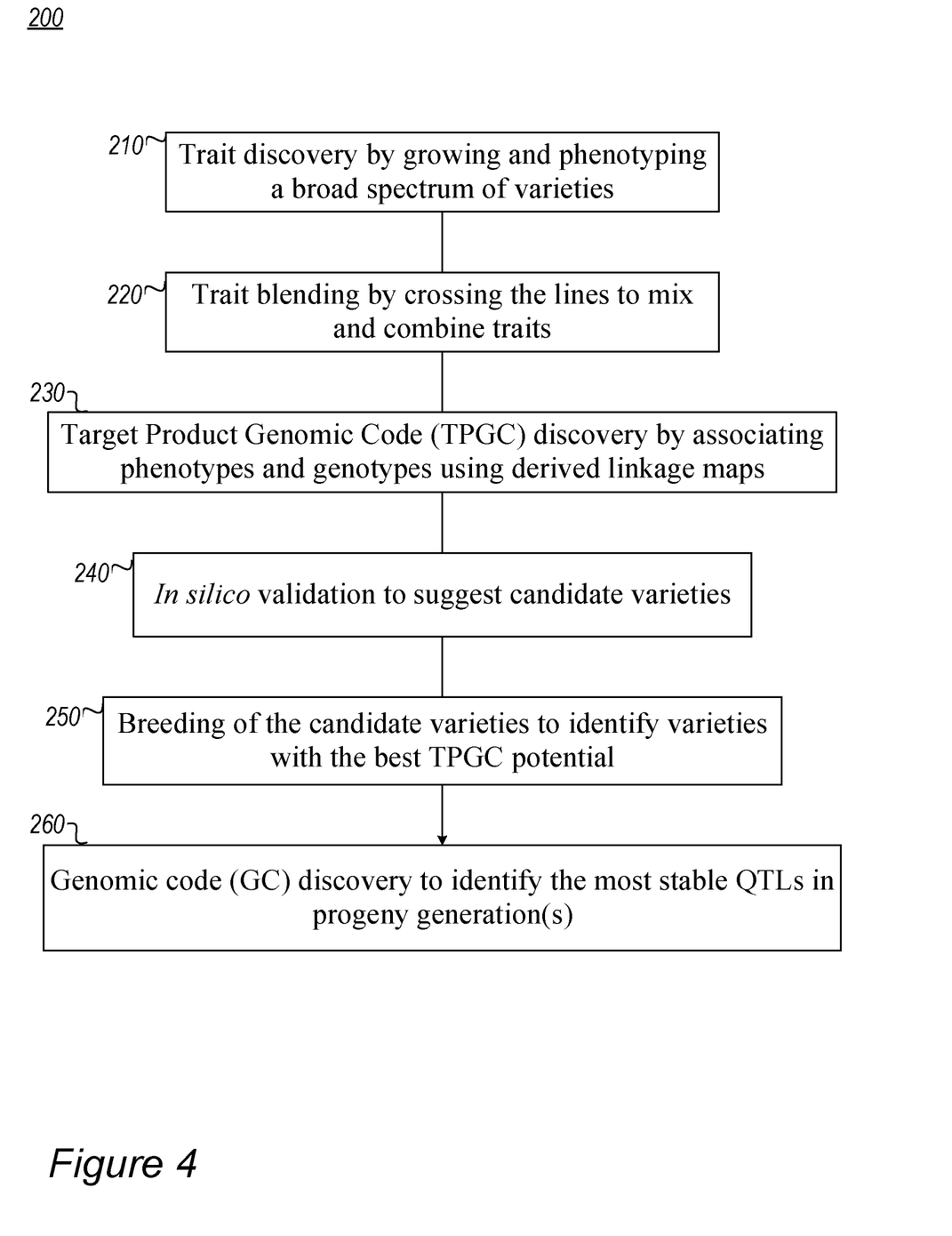
FIG. 4 is a high-level schematic illustration of the breeding method, according to some embodiments of the invention.

FIG. 4 is a high-level schematic illustration of a breeding method 200, according to some embodiments of the invention. Breeding method 200 comprises stages of trait discovery by growing and phenotyping a broad spectrum of varieties (stage 210), trait blending by developing hybridized lines through crossing the selected lines to mix and combine traits and selfing of the progeny in subsequent generations (stage 220), target Product Genomic Code (TPGC) discovery by associating phenotypes and genotypes using derived linkage maps (stage 230), in silico validation to suggest candidate varieties (stage 240), breeding of the candidate varieties to identify varieties with the best TPGC potential (stage 250) and genomic code (GC) discovery to identify the most stable QTLs in hybridized progeny generation(s) (stage 260), as explained in detail below.

In embodiments, sesame lines were bred to reach high yield levels by collecting various sesame lines worldwide, creating F2 linkage populations, applying intensive phenotyping and genotyping of thousands of sesame lines, predicting of QTL's affecting the yield level trait, and establishing unique marker combinations, termed "marker cassettes" herein, to characterize novel high yield lines found by the method and not existing in commercial or natural lines.

The breeding methodology was based on algorithms for deriving the Target Product Genomic Code (TPGC) to associate (i) the Target Product (TP) being defined in advance based on market requirements and including a set of desired attributes (traits) that are available in natural genetic variations; and (ii) the Genomic Code (GC) comprising set(s) of genomic regions that include quantitative trait loci (QTLs) that affect and are linked to the TP traits. The algorithms may be configured to calculate multiple genomic interactions and to maximize the genomic potential of specific plants for the development of new varieties. The breeding program was constructed to derive the TPGC, and then by crossing and selfing to achieve a product which contains the specific GC that corresponds to the required TPs.

Certain embodiments of the breeding process of developing hybridized lines, through crossing and successive generations of selfing comprise stages such as: (i) Trait Discovery, in which a broad spectrum of varieties from different geographies and worldwide sources are grown and phenotyped in order to discover new traits that can potentially be combined to create a new product; (ii) Trait Blend, in which a crossing cycle is carried out based on phenotypic assumption(s), in which the different traits are mixed and combined. Initial trait cycle(s) are followed by additional cycle(s) to create F2 (and possibly higher generations) population(s) that provide the basis for algorithmic analysis for constructing the TPGC; (iii) TPGC Discovery, in which the plant(s) are phenotyped and genotyped to produce linkage map(s), discovering the relevant QTLs and deriving the TPGC; (iv) several line validation stages over several years in which sesame lines based on millions of in silico calculated variations (and/or selections) are grown and are used to defined the initial varieties; (v) Trait TPGC Blend, in which accurate crossings are performed in order to calculate the most efficient way to reach the best TPGC. The crossings are performed after in silico selection from millions of combinations, and are based, at least on part on phenotype assumptions; and (vi) Consecutive algorithm-based GC discovery stage(s) applied to F2 (or higher generation) population(s) grown in additional cycle(s).

Defining the TP for high yield shatter-resistant sesame varieties includes the development of high throughput methods for high yield level identification.

In the following non-limiting example of the process, Trait Discovery (i) was based on propriety germplasm including hundreds of elite varieties and thousands of F2 individual plants and also 219 different sesame lines that were obtained from the U.S. National Plant Germplasm System (NPGC) and courtesy of professor Amram Ashri sesame germplasm collection (see Ashri, A. 1998, Sesame Breeding. In: Janick J. (ed.), Plant Breeding Reviews Vol. 16. John Wiley and Sons, Somerset, N.J., pp. 179-228). These lines were used for the Trait Blend stage (ii), with crosses executed based on the potential for enrichment of genomic diversity to create new complex(es) of traits for the high yield level as the initial step for the TP-directed breeding program for high yield sesame lines. The resulted F1 hybrids were later self-crossed to create F2 linkage populations that showed phenotypic segregation. The F2 population were then planted in three different environments for discovering the TPGC (iii) that includes high yield traits. After screening 2500 individuals, a set of ca. 300 representatives was selected. The selected individuals F2 was massively phenotyped for traits associated with yield, as detailed in the following. The measurement results were summarized into the representative high yield level trait.

TPGC Discovery (iii) included genotyping ca. 2500 selected individual plants from six populations. The Analysis was performed with a panel of 612 markers based on single nucleotide polymorphism (SNP) and directly designed based on the polymorphism found in the parental lines of the populations which were analyzed in depth using high throughput DNA sequencing technologies The Panel was designed to maximize the chance to have the largest number of common segregate SNP's in order to create highly similar linkage maps for all observed populations. The computation of linkage maps was executed on each linkage F2 population based on the genotyping results. Linkage maps were computed with MultiPoint, an interactive package for ordering multilocus genetic maps, and verification of maps based on resampling techniques. Discovery of QTLs that are related to high yield level was carried out with the MultiQTL package, based on the linkage maps that were merged by Multipoint and the F2 population phenotype data, and using multiple interval mapping (MIM). MultiQTL significance was computed with permutation, bootstrap tools and FDR (false discovery rate) for total analysis. The linkage maps of all six F2 populations and the information of the high yield level traits over all genotyped plants belonging to those populations were analyzed and used to predict the QTLs in a "one trait to one marker" model, in which for all markers that constructed the linkage maps, each trait was tested independently against each one of the markers. In the provided examples, altogether seven markers were found to be related to yield and traits associated with yield components (see Table 1 above), with one marker common to all high yield populations.

In general, the populations presented different markers that related to high yield levels. However, subsets of common markers were found to be shared by multiple populations and are referred to herein as marker cassettes. The significance and co-occurrences of the high yield level markers were evaluated using an algorithm that related the genotype-phase of each marker to respective QTLs and traits in linkage F2 in each population, for populations in different environments. The occurrence of high yield level markers in two or more linkage F2 population (repetitive markers) strengthened its significance as representative for high yield level QTL.

Following TPGC Discovery (iii), an in-silico breeding program (iv) was established to process the TPGC blend (including combinations of QTLs for different plants) to simulate and predict the genotypic states of self, cross-self and hybrid plant with respect to the QTLs and their predicted effects on each phase of the markers for the high yield level trait. The in-silico breeding program was constructed to yield millions of in silico selfing combinations which were bred and then evaluated up to F8—to measure the potential for each of the genotyped plants to acquire the high yield level in the right combination at the right phase. The analysis resulted in identifying ca. 300 plants having the highest score for high yield level, which were thus chosen for the actual selfing and cross-selfing procedures. Under this procedure, QTLs from different population were combined to yield plants containing new and unique cassettes of QTLs and yielding high yield levels.

The high yield sesame lines were then validated as retaining the trait in the following generations by genotyping the offspring to verify they maintain the identified marker cassettes. Specifically, the parental lines of linkage F2 populations together with 220 different sesame cultivars (landraces and old commercial varieties) were genotyped based on high yield level markers of all populations. The cassettes detailed in Table 1 were found to wholly differentiate the developed high yield lines and the rest of the sesame cultivars screened.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A hybrid sesame plant or a part thereof, the sesame plant having a high yield and shatter-resistant capsules and comprising:

a plurality of quantitative trait loci (QTLs), the QTLs having a corresponding plurality of nucleic acid genetic markers that are associated with a plurality of phenotypic traits of the hybrid sesame plant, wherein the plurality of phenotypic traits comprise at least a Number of capsules per leaf axil trait, a Capsule length trait, a Number of lateral shoots trait and a Height to first capsule trait, wherein the QTL associated with the Number of capsules per leaf axil trait comprise QTL 4 with corresponding nucleic acid markers of SEQ ID NQs: 7-8 on chromosome 7, and wherein the sesame plant or part thereof is homozygous with respect to SEQ ID NO: 7 or heterozygous at QTL 4;

wherein the QTLs associated with the Capsule length trait comprise QTLs 1, 3 with corresponding nucleic acid markers of SEQ ID NOs: 1-2, 5-6 on chromosome 9, respectively, and QTL2 with corresponding nucleic acid markers of SEQ ID NO: 3-4 on chromosome 6, wherein the sesame plant or part thereof is homozygous at SEQ ID NO: 1, 3 and 5 or heterozygous at QTL1, QTL2 and QTL3.

2. The hybrid sesame plant or part thereof according to claim 1, wherein:
the QTL associated with the Number of capsules per leaf axil trait comprise QTL 3 with corresponding markers of SEQ ID NO: 5-6 on chromosome 9, and wherein the sesame plant or part thereof is homozygous with respect to SEQ ID NO: 5 or heterozygous at QTL 3.

3. The hybrid sesame plant or part thereof according to claim 1, wherein:
the QTLs associated with the Capsule length trait and with the Height to first capsule trait comprise QTL5 with corresponding nucleic acid markers of SEQ ID NO: 9-10 on chromosome 3, and QTL6 with corresponding markers of SEQ ID NO: 11-12 on chromosome 9, and
the QTL associated with number of lateral shoots comprise QTL7 with corresponding nucleic acid markers of SEQ ID NO: 13-14 on chromosome 9, wherein
the sesame plant or part thereof is homozygous with respect to SEQ ID NO: 9, 11 and 13 or heterozygous at QTL 5, QTL6, and QTL7.

4. The hybrid sesame plant or a part thereof according to claim 1, wherein the phenotypic traits further comprise a high yield of at least ten percent more than control sesame lines ES103, ES107 and ES108.

5. The hybrid sesame plant or a part thereof according to claim 1, wherein the part thereof is any of: a seed, an endosperm, an ovule, pollen, cell, cell culture, tissue culture, plant organ, protoplast, meristem, embryo, or a combination thereof.

6. A hybrid sesame plant or a part thereof, the sesame plant having shatter-resistant capsules and comprising: a plurality of quantitative trait loci (QTLs), the QTLs having a corresponding plurality of nucleic acid genetic markers that are associated with a plurality of phenotypic traits of the sesame plant, wherein:
the phenotypic traits comprise at least a Number of capsules per leaf axil trait, a Capsule length trait and a Height to first capsule trait,
the QTL associated with the Number of capsules per leaf axil trait comprise QTL 4 with corresponding markers of SEQ ID NO: 7-8,
the QTLs associated with the Capsule length trait comprise QTL1 and QTL3 with corresponding nucleic acid markers of SEQ ID NOs: 1-2 and SEQ ID NO: 5-6, respectively, on chromosome 9, and QTL2 with corresponding nucleic acid markers of SEQ ID NO: 3-4 on chromosome 6,
the QTLs associated with the Height to first capsule trait comprise QTL1 and QTL3 with corresponding nucleic acid markers of SEQ ID NO: 1-2 and SEQ ID NO: 5-6, respectively, on chromosome 9,
optionally, the phenotypic traits further comprise a Number of lateral shoots trait, wherein
the sesame plant or part thereof is homozygous with respect to SEQ ID NO: 1, SEQ ID NO: 3, SEQ ID NO: 5, and SEQ ID NO: 7, or heterozygous at QTL 1, QTL2, QTL3 and QTL4.

7. The hybrid sesame plant or a part thereof according to claim 6, wherein the phenotypic traits comprise a high yield of at least ten percent more than control sesame lines ES103, ES107 and ES108.

8. The hybrid sesame plant or a part thereof according to claim 6, wherein the part thereof is any of: a seed, an endosperm, an ovule, pollen, cell, cell culture, tissue culture, plant organ, protoplast, meristem, embryo, or a combination thereof.

9. A hybrid sesame plant or a part thereof, the sesame plant having shatter-resistant capsules and comprising:
a plurality of quantitative trait loci (QTLs), the QTLs having a corresponding plurality of nucleic acid genetic markers that are associated with a plurality of phenotypic traits of the sesame plant, wherein:
the phenotypic traits comprise at least a Number of capsules per leaf axil trait, a Capsule length trait, a Number of lateral shoots trait and a Height to first capsule trait,
the QTL associated with the Number of capsules per leaf axil trait comprise QTL 4 with corresponding nucleic acid markers of SEQ ID NO: 7-10 on chromosome 9,
the QTLs associated with the Capsule length trait, with the Height to first capsule trait and with the Number of lateral shoots trait comprise QTLs 5, 6, 7 with corresponding nucleic acid markers of SEQ ID NOs: 9-10, SEQ ID NOs: 11-12, SEQ ID NOs: 13-14, respectively,
the sesame plant or part thereof is homozygous with respect to SEQ ID NO: 6, SEQ ID NO: 7, SEQ ID NO: 9 and SEQ ID NO: 13 or heterozygous at QTL 4, QTL5, QTL6 and QTL7.

10. The hybrid sesame plant or a part thereof according to claim 9, wherein the phenotypic traits comprise a high yield of at least ten percent more than control sesame lines ES103, ES107 and ES108.

11. The hybrid sesame plant or a part thereof according to claim 9, wherein the part thereof is any of: a seed, an endosperm, an ovule, pollen, cell, cell culture, tissue culture, plant organ, protoplast, meristem, embryo, or a combination thereof.

* * * * *

SEQUENCE LISTING

<160> NUMBER OF SEQ ID NOS: 14

<210> SEQ ID NO 1
<211> LENGTH: 160
<212> TYPE: DNA

<213> ORGANISM: Sesamum indicum

<400> SEQUENCE: 1

| | | | | | |
|---|---|---|---|---|---|
| ctatctttgt | gataatccta | taaattaaac | aaaaatacca | ttgactattg | agattagaga | 60 |
| aagatgcaat | ttaactcatc | taatatgaga | aatgagtaaa | agtgttatga | taatttgcta | 120 |
| attccttttt | tgcactggtt | tatctgctca | tttcacatat | | | 160 |

<210> SEQ ID NO 2
<211> LENGTH: 160
<212> TYPE: DNA
<213> ORGANISM: Sesamum indicum

<400> SEQUENCE: 2

| | | | | | |
|---|---|---|---|---|---|
| ctatctttgt | gataatccta | taaattaaac | aaaaatacca | ttgactattg | agattagaga | 60 |
| aagatgcaat | ttaactcatg | taatatgaga | aatgagtaaa | agtgttatga | taatttgcta | 120 |
| attccttttt | tgcactggtt | tatctgctca | tttcacatat | | | 160 |

<210> SEQ ID NO 3
<211> LENGTH: 201
<212> TYPE: DNA
<213> ORGANISM: Sesamum indicum

<400> SEQUENCE: 3

| | | | | | |
|---|---|---|---|---|---|
| agttttttgtt | cttaaacagt | gcatttttt | tttttttgac | aaaattcatt | attttcatta | 60 |
| tcttgctgtc | aaatataatg | aaaaaattca | tctgaggctg | ttttgagggt | gggaaagaaa | 120 |
| aactatcatt | tcctccctga | aatttaattt | tttgaatatt | taatcatatt | cggacaggtg | 180 |
| atattttcac | ataaaagcaa | t | | | | 201 |

<210> SEQ ID NO 4
<211> LENGTH: 201
<212> TYPE: DNA
<213> ORGANISM: Sesamum indicum

<400> SEQUENCE: 4

| | | | | | |
|---|---|---|---|---|---|
| agttttttgtt | cttaaacagt | gcatttttt | tttttttgac | aaaattcatt | attttcatta | 60 |
| tcttgctgtc | aaatataatg | aaaaaattca | tctgaggctg | ctttgagggt | gggaaagaaa | 120 |
| aactatcatt | tcctccctga | aatttaattt | tttgaatatt | taatcatatt | cggacaggtg | 180 |
| atattttcac | ataaaagcaa | t | | | | 201 |

<210> SEQ ID NO 5
<211> LENGTH: 201
<212> TYPE: DNA
<213> ORGANISM: Sesamum indicum

<400> SEQUENCE: 5

| | | | | | |
|---|---|---|---|---|---|
| aacacaaaaa | accaaacact | ttcatatgat | catagttagg | ggccttctta | tataataatt | 60 |
| catagggtgt | tttccaactt | aatgtttgtg | ttggaagtct | attaattatg | tatgtggcag | 120 |
| ctaacaatgc | ctcggcccag | aatctttgtg | gcatgtttgc | ttggaacatc | aaagatctag | 180 |
| ccccttgaaa | aaggtgttgg | t | | | | 201 |

<210> SEQ ID NO 6
<211> LENGTH: 201
<212> TYPE: DNA
<213> ORGANISM: Sesamum indicum

<400> SEQUENCE: 6

```
aacacaaaaa accaaacact ttcatatgat catagttagg ggccttctta tataataatt    60
catagggtgt tttccaactt aatgtttgtg ttggaagtct gttaattatg tatgtggcag   120
ctaacaatgc ctcggcccag aatctttgtg gcatgtttgc ttggaacatc aaagatctag   180
ccccttgaaa aaggtgttgg t                                             201
```

```
<210> SEQ ID NO 7
<211> LENGTH: 160
<212> TYPE: DNA
<213> ORGANISM: Sesamum indicum

<400> SEQUENCE: 7
atttggagcc gggttcacat tgtttccagc ctctcaaagg attttggtct tccaggattc    60
aggatcggca tgatctattt caacagtaaa accctgattg ctgctgcaac aaaaatgtcg   120
agttttgggc tggtctcttc tcaatcccag ttcctactgt                         160

<210> SEQ ID NO 8
<211> LENGTH: 160
<212> TYPE: DNA
<213> ORGANISM: Sesamum indicum

<400> SEQUENCE: 8
atttggagcc gggttcacat tgtttccagc ctctcaaagg attttggtct tccaggattc    60
aggatcggca tgatctattc caacagtaaa accctgattg ctgctgcaac aaaaatgtcg   120
agttttgggc tggtctcttc tcaatcccag ttcctactgt                         160

<210> SEQ ID NO 9
<211> LENGTH: 198
<212> TYPE: DNA
<213> ORGANISM: Sesamum indicum

<400> SEQUENCE: 9
ttaaagtgat gagagttgat gttactgaga atataaatga ggatactgtg aagcagttta    60
tcgaagaaga caatgagaac acaaccagca aggacaccaa agaggaagtt actgatatgg   120
gtaacaatca gccagatcga gttgctgcac aaggagataa tgatgtgatg gaagatgaaa   180
ataatttaga catgaagc                                                 198

<210> SEQ ID NO 10
<211> LENGTH: 198
<212> TYPE: DNA
<213> ORGANISM: Sesamum indicum

<400> SEQUENCE: 10
ttaaagtgat gagagttgat gttactgaga atataaatga ggatactgtg aagcagttta    60
tcgaagaaga caatgagaac acaaccagca aggacaccga agaggaagtt actgatatgg   120
gtaacaatca gccagatcga gttgctgcac aaggagataa tgatgtgatg gaagatgaaa   180
ataatttaga catgaagc                                                 198

<210> SEQ ID NO 11
<211> LENGTH: 201
<212> TYPE: DNA
<213> ORGANISM: Sesamum indicum

<400> SEQUENCE: 11
atcatgaatt ttactcctat tttttttgtta atattaacaa atctagtgga ttttgactaa    60
```

```
caaagggact tattttatta aacgaaagca accttcaagg atattaaata taatttttca      120
aaccacatga gatttatatg caattacatt aaatttcggt agagtggagt agttatccct      180
agaaatatta cagtcgaagt g                                                201

<210> SEQ ID NO 12
<211> LENGTH: 201
<212> TYPE: DNA
<213> ORGANISM: Sesamum indicum

<400> SEQUENCE: 12
atcatgaatt ttactcctat ttttttgtta atattaacaa atctagtgga ttttgactaa       60
caaagggact tattttatta aacgaaagca accttcaagg gtattaaata taatttttca      120
aaccacatga gatttatatg caattacatt aaatttcggt agagtggagt agttatccct      180
agaaatatta cagtcgaagt g                                                201

<210> SEQ ID NO 13
<211> LENGTH: 301
<212> TYPE: DNA
<213> ORGANISM: Sesamum indicum

<400> SEQUENCE: 13
ggaggcaaaa gaatacgggt tggttgatgc agtgatcgat gatggcaagc ctggactagt       60
cgcacccatc gcagatactg cacccccacc aaaaacccgt gtctgggatc tttggaaaat      120
cgaaggcagt aaaaaagcca agaaaaactt accctccgaa gagaaactat tacaaaatgg      180
atacacagtt ggccaaggtg aagatgacag aagcacggaa caggtagagg aagcaccaac      240
atctcaatga gtaatgaatg ttgagatatt tcttgtatac actgtcaaac attgtagcta      300
g                                                                      301

<210> SEQ ID NO 14
<211> LENGTH: 301
<212> TYPE: DNA
<213> ORGANISM: Sesamum indicum

<400> SEQUENCE: 14
ggaggcaaaa gaatacgggt tggttgatgc agtgatcgat gatggcaagc ctggactagt       60
cgcacccatc gcagatactg cacccccacc aaaaacccgt gtctgggatc tttggaaaat      120
cgaaggcagt aaaaaagcca agaaaaactt gccctccgaa gagaaactat tacaaaatgg      180
atacacagtt ggccaaggtg aagatgacag aagcacggaa caggtagagg aagcaccaac      240
atctcaatga gtaatgaatg ttgagatatt tcttgtatac actgtcaaac attgtagcta      300
g                                                                      301
```